(12) United States Patent
Zhang et al.

(10) Patent No.: US 9,848,867 B2
(45) Date of Patent: Dec. 26, 2017

(54) NON-INVASIVE SUTURE ANCHOR AND METHOD

(75) Inventors: Renwen Zhang, Wayne, NJ (US); Twana Davisson, Montclair, NJ (US); Jeffrey Spalazzi, Fair Lawn, NJ (US); Venkat R. Garigapati, Southborough, MA (US); Matthew E. Murphy, Wexford (IE); Anthony P. Napolitano, Chappaqua, NY (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 1097 days.

(21) Appl. No.: 13/880,674

(22) PCT Filed: Nov. 16, 2011

(86) PCT No.: PCT/US2011/060956
§ 371 (c)(1),
(2), (4) Date: Apr. 19, 2013

(87) PCT Pub. No.: WO2012/071227
PCT Pub. Date: May 31, 2012

(65) Prior Publication Data
US 2013/0238027 A1 Sep. 12, 2013

Related U.S. Application Data

(60) Provisional application No. 61/416,406, filed on Nov. 23, 2010.

(51) Int. Cl.
A61B 17/04 (2006.01)
A61B 17/00 (2006.01)
A61B 17/06 (2006.01)

(52) U.S. Cl.
CPC .... *A61B 17/0401* (2013.01); *A61B 17/00491* (2013.01); *A61B 17/06166* (2013.01); *A61B 2017/0404* (2013.01); *A61B 2017/0412* (2013.01); *A61B 2017/0414* (2013.01)

(58) Field of Classification Search
CPC .................................................. A61B 17/0401
See application file for complete search history.

(56) References Cited

U.S. PATENT DOCUMENTS

| 5,988,171 | A | 11/1999 | Sohn et al. | |
|---|---|---|---|---|
| 6,331,312 | B1 * | 12/2001 | Lee | A61F 2/28 424/422 |
| 2001/0051815 | A1 * | 12/2001 | Esplin | A61B 17/0401 606/232 |

(Continued)

OTHER PUBLICATIONS

Vo-Dinh, Nanotechnology in Biology and Medicine, CRC Press (Jan. 24, 2007) [retrieved on Feb. 8, 2012] entire document retrieved form the Internet: <URL:http://books.google.com/books/about/Nanotechnolgy_in_biology_and_medicine.html?id=t91Pt1Hu6bAC>, (1 page).*

(Continued)

*Primary Examiner* — Diane Yabut
(74) *Attorney, Agent, or Firm* — Lando & Anastasi LLP

(57) ABSTRACT

A non-invasive device for anchoring a suture includes a sheet to which a suture can be attached and an adhesive that can affix the sheet to bone. The method provides placing effective amount of an adhesive on a bone and attaching the suture to the adhesive and allowing the adhesive to set.

17 Claims, 4 Drawing Sheets

(56) References Cited

U.S. PATENT DOCUMENTS

| | | | |
|---|---|---|---|
| 2006/0089646 A1* | 4/2006 | Bonutti | A61B 17/0218 |
| | | | 606/279 |
| 2009/0258966 A1* | 10/2009 | Hirayama | A61K 6/0023 |
| | | | 523/118 |
| 2010/0121459 A1* | 5/2010 | Garigapati | A61K 35/32 |
| | | | 623/23.61 |
| 2011/0082498 A1* | 4/2011 | Deslauriers | A61B 17/00491 |
| | | | 606/214 |
| 2011/0277931 A1* | 11/2011 | Garigapati | A61L 27/425 |
| | | | 156/331.6 |

OTHER PUBLICATIONS

International Search Report and Written Opinion dated Feb. 21, 2012 for International Application No. PCT/US2011/060956 (12 pages).

(Vo-Dinh) Nanotechnology in Biology and Medicine, CRC Press (Jan. 24, 2007) [retrieved on Feb. 8, 2012] entire document retrieved from the Internet: <URL:http://books.google.com/books/aboutNanotechnology_in_biology_and_medicine.html?id=t91Pt1Hu6bAC>, (1 page).

* cited by examiner

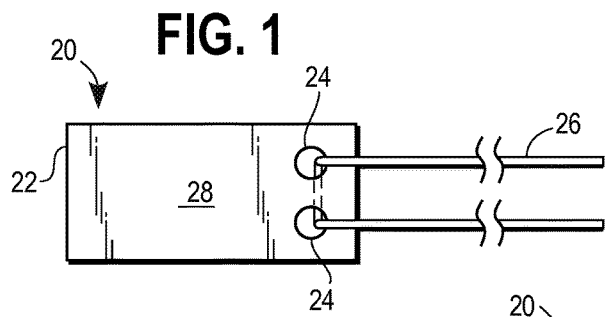
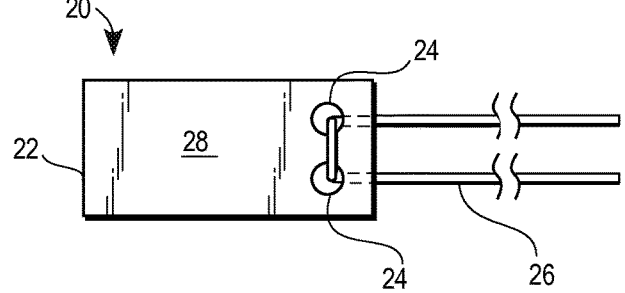
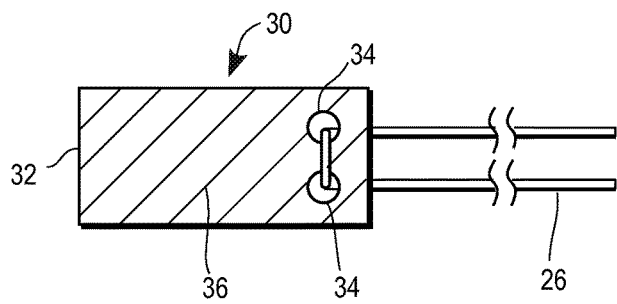
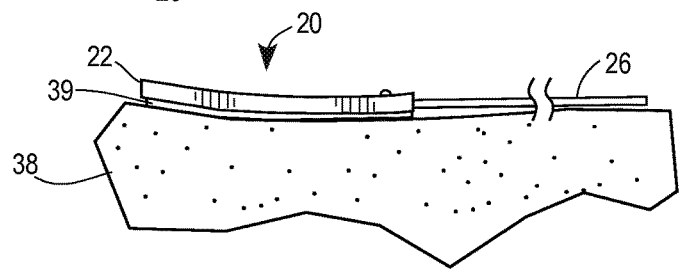
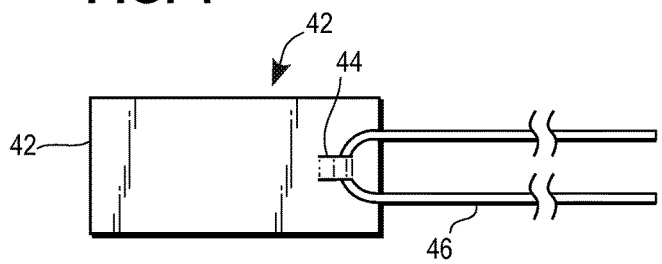
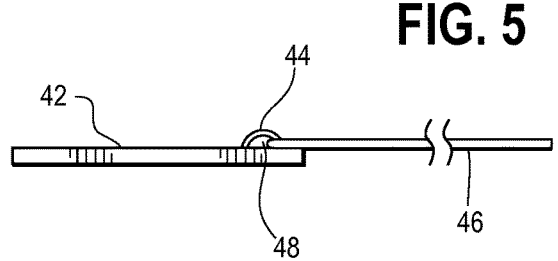

FIG. 7
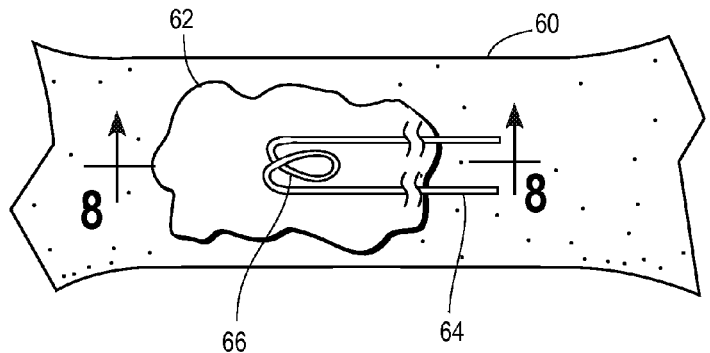
FIG. 7a
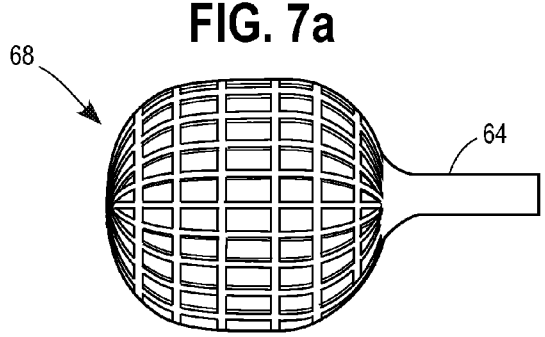
FIG. 7b
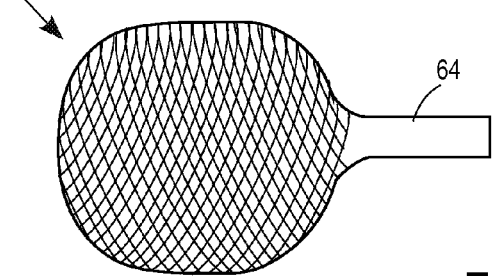
FIG. 7c
FIG. 7d
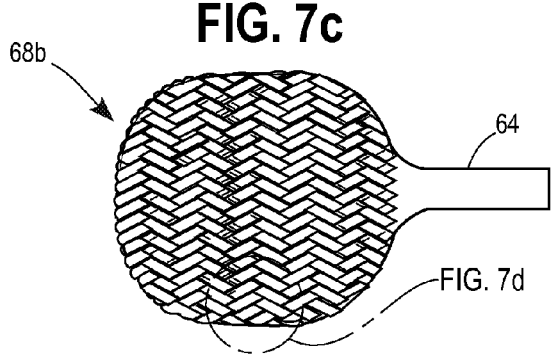
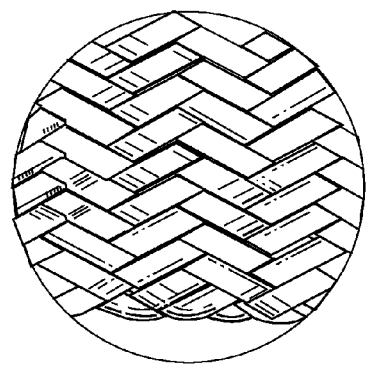

NON-INVASIVE SUTURE ANCHOR AND METHOD

CROSS REFERENCE TO RELATED APPLICATIONS

The present application is a national phase entry of International Application No. PCT/US2011/060956, filed on Nov. 16, 2011, which claims the benefit of U.S. Provisional Application No. 61/416,406, filed on Nov. 23, 2010. The entire contents of each of which is incorporated herein by reference.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

This invention relates to suture anchors and more particularly to suture anchors and methods of using suture anchors that can attach soft tissue to bone and are also minimally invasive to bone.

2. Description of the Background of the Invention

During various surgical procedures, it is often necessary to attach soft tissues, like a ligament or tendon, to bone. Typically the suture is anchored in to the bone using a suture anchor that is drilled or sometimes punched or stapled into the bone. Sutures also can be anchored by placing a suture into a predrilled hole in the bone that is also filled with an adhesive material such as disclosed in U.S. Pat. No. 5,665,110.

For patients with compromised bone structure, such as elderly patients, that have ruptured a tendon or ligament, the poor quality of the bone structure due to osteoporosis or osteopenia can limit the effectiveness of prior systems of anchoring sutures to bone. If the suture anchor is subject to being pulled out of the bone before the soft tissue has a chance to fully heal there can be clinical failure of the procedure and the patient must undergo a follow on procedure or suffer with decrease mobility or range of motion. Prior attempts to remedy this issue have focused on using larger diameter anchors to increase the pull out resistance or other methods of fixation such as double row repairs which require additional anchors or massive cuff stitching.

SUMMARY OF THE INVENTION

One embodiment of the present disclosure comprises a method of affixing a suture to bone in a minimally invasive manner that includes the steps of applying an effective amount of an adhesive to the outer surface of a bone, attaching a suture to the adhesive and allowing the adhesive to set.

A further embodiment of the present disclosure comprises a suture anchor that can be adhesively attached to the surface of bone comprising a relatively flat sheet and a suture attached to the sheet.

A still further embodiment of the present disclosure comprises a kit for attaching a suture to bone that includes a suture and a calcium phosphate bone adhesive that when set has a separation force of greater than 30 N.

BRIEF DESCRIPTION OF THE DRAWINGS

FIG. 1 is a plan view of the top of one embodiment of the suture anchor of the present disclosure;

FIG. 2 is a plan view of the bottom of the embodiment of FIG. 1;

FIG. 3 is a plan view of the bottom of the embodiment of FIG. 1 showing an alternative embodiment;

FIG. 3a is a side view of the embodiment of FIG. 1 showing the suture anchor attached to bone;

FIG. 4 is a plan view of the top of a second embodiment of a suture anchor;

FIG. 5 is a side view of the embodiment of FIG. 4;

FIG. 7 is a view of a suture attached to bone using one embodiment of the method of the present disclosure;

FIGS. 7a-c show alternate arrangements for the embodiment shown in FIG. 7;

FIG. 7d is an enlargement of a portion of the embodiment of FIG. 7c to show detail;

DETAILED DESCRIPTION OF THE PREFERRED EMBODIMENTS

Figure 6:
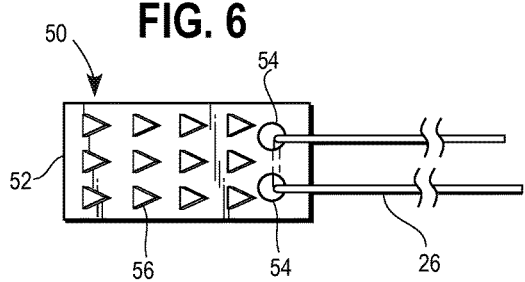
FIG. 6 is a plan view of the bottom of a further alternative embodiment of the suture anchor of the present disclosure.

With reference to FIGS. 1 and 2, a suture anchor 20 has a relatively flat sheet 22. Sheet 22 can be formed from a wide range of biocompatible materials including titanium, titanium alloys, ferrous alloys, cobalt-chromium alloys, degradable metals, biocompatible polymers, bioceramics, or composites of polymer and ceramics. Examples of biocompatible polymers include but are not limited to poly (ether-ether ketone), poly (L-lactide), poly (D,L-lactide), polyglycolide, polycaprolactone, poly(tetramethylglycolic acid), poly(hydroxybutyrate), poly(hydroxyvalerate), poly (L-lactide-co-glycolide), poly(D,L-lactide-co-glycolide), poly(glycolide-co-trimethylenecarbonate), poly(glycolide-co-caprolactone), poly(dioxanone), poly(glycolide-co-dioxanone-co-trimethylene-carbonate), poly(glycolide-co-caprolactone-co-L-lactide-co-trimethylene-carbonate), poly (hydroxybutyrate-co-hydroxyvalerate), poly(methylmethacrylate), poly(acrylates), polyamines, polyamides, polyimidazoles, polynitriles, poly(vinyl-pyrrolidone), collagen, silk and keratin, chitin, a combination thereof, or a copolymer thereof. The polymer structure can be linear, block, branched, hyperbranched or star shaped polymers. Examples of bioceramics include but are not limited to hydroxyapatite, β-tricalcium phosphate, tetracalcium phosphate, biphasic calcium phosphate, nanocrystalline hydroxyapatite, bioactive glass, 45S5 bioactive glass, titanium oxide, aluminum oxide. Composites may consist of any combination of any one or more of the above mentioned biocompatible polymers with any one or more of the above mentioned bioceramics. Sheet 22 can be any suitable thickness, size or shape and in some embodiments sheet 22 can be sufficiently flexible or malleable to conform to the shape of the bone surface to which the suture anchor 20 is to be affixed. Sheet 22 has at least 1 hole 24 passing through sheet 22 so that a suture 26 can pass through these holes as shown. Even though 2 holes are shown in the figures, in some embodiments a single hole may be all that is required. The only requirement for sheet 22 is that sheet 22 be sufficiently strong or robust so that the suture 26 will not rupture the area of sheet 22 between holes 24 at pressures that suture 26 will encounter during normal patient activity. Additional holes 24 can be placed in sheet 22 and these holes will allow the suture 26 to be place in different positions for different procedures. Also, these added holes 24 can also assist the formation of the bond of sheet 22 to the bone formed by the adhesive as the adhesive can penetrate the holes 24 to further lock the sheet 22 in place and increase purchase or removal force. In one embodiment, the sheet 22 has a size of 5 mm by 8 mm, however larger or smaller sheets 22 can be used depending on the clinical need or the procedure.

The front and rear surfaces 28 of sheet 22 can be either smooth as shown in FIGS. 1 and 2 or as shown in FIG. 3, an alternative embodiment of a suture anchor 30 has a sheet 32 formed from similar materials to sheet 22 but one or both of the surfaces of sheet 32 have grooves 36 or other roughening the surface of the sheet 32 to further enhance adhesion of the sheet 32 to the bone by the adhesive. Sheet 32 also includes at least two holes 34 that can be used to attach suture 26 to sheet 32.

As noted above, the sheet 22 or 32 is adhered to the underlying bone 38 by an adhesive material 39 as shown in FIG. 3a. The adhesive materials 39 can be applied directly to the bone 38 or to the back of sheet 22 or 32 prior to the plate 22 or 32 being placed near the bone 38. Also, as noted above, the sheet 22 or 32 can be somewhat flexible or malleable so that the sheet 22 can conform to the shape of the bone as shown in FIG. 3a.

Suitable adhesives include the calcium phosphate bone cements. It has been found that tetra calcium phosphate (TTCP) has unusual properties not shared by other calcium phosphate compositions. TTCP is the most basic of all the calcium phosphates; therefore, it readily reacts to acidic compounds. While other calcium phosphate compositions can be used in addition to the TTCP, the compositions must include an effective amount of TTCP. The TTCP used in the present compositions can be made by a variety of methods. The TTCP can be 100% pure material or can include other calcium and calcium phosphate materials as an impurity, e.g. α-TCP, CaO and/or HA.

A second component that can be included in the compositions is a compound that has the following formula;

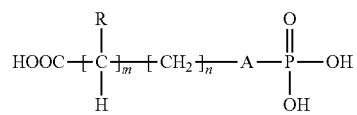

where A is O, $CH_2$, or S; R is H, $NH_2$, $NHCO(CH_2)_tCH_3$ where t is 0 to 2, $NH(CH_2)_xCH_3$ where x is 0 to 3, NR1R2 where R1 is $(CH_2)_yCH_3$ and R2 is $(CH_2)_yCH_3$ where y is 0 to 2, $(CH_2)_zCH_3$ where z is 0 to 3, where m is 0 to 1, and where n is 0 to 3. Preferred compounds are those where A is O or $CH_2$, R is H or $NH_2$, m is 0 or 1 and n is 0 or 1. The most preferred compound is phosphoserine that has the following structure;

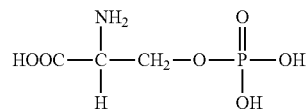

The compounds that are structurally similar to phosphoserine, which contain the reactive phosphonate or phosphate, and which have COOH functional groups, are capable of interacting with the $Ca^+$ within the TTCP to form a calcium based matrix and are referred to as compounds structurally similar to phosphoserine in this description. The combination of these functional groups plus the geometry such as the chain length between the phosphorous and the COOH are unique aspects to the molecules which affect the level of adhesive bonding strength to substrate surfaces such as bone and metal.

The preferred compound that is structurally similar to phosphoserine is phosphoserine which may be any form of phosphoserine, including the phospho-D-serine, phospho-L-serine or the phospho-DL-serine forms may be used. The stereochemistry of the phosphoserine does not seem to have any impact on the properties of the compositions disclosed herein.

It has been found that when the quantity of compounds that are structurally similar to phosphoserine is increased beyond about 10% w/w of the combination of the compound and the TTCP, more generally in the range of about 10% to about 90%, more typically in the range of 15% to about 50%, or preferably from about 20% to about 40%, the tack and adhesion properties of the resulting compositions were significant. At such levels, the influence of compounds that are structurally similar to phosphoserine extends beyond internal interaction with the cement, but also extends to significant binding with the hydroxyapatite architecture and proteins of bone. At below about 10% by weight of the compound structurally similar to phosphoserine, the compositions do not have a tacky state and these compositions do not have adhesive properties.

The compositions as described herein have many unique properties not found in prior calcium phosphate compositions. One particularly important property is that the compositions have a tacky state immediately subsequent to mixing with an aqueous medium. This tack property is retained for a number of minutes, sometimes up to 12 minutes depending on the application requirement, typically up to about 4 minutes, and preferably up to about 2 minutes, after mixing with the aqueous medium. The time of the tacky state is dependent on a number of factors including relative ratio of the components, the particle sizes of the component materials, the presence of additives and the like. During this time the compositions will adhere bone to bone and bone to other materials, often without the need for external clamping or other application of pressure. The tacky state is not so aggressive that the composition will permanently affix the materials together at this point in time. Rather the tacky state can allow the materials to be moved relative to each other and also to be re-opposed without appreciable loss of ultimate cured strength. This is important in a medical setting so that the user can make sure the bone and the other material to be adhered to the bone are in the proper position relative to each other.

The tacky state is followed by a putty state. In the putty state, the tacky property has substantially disappeared and the compositions can be shaped or sculpted. In addition, during the putty state, the composition can be formed into shapes or used to fill voids in bone in a manner similar to putty. This putty state is retained for a number of minutes, sometimes up to 15 minutes depending on the application requirement, typically up to about 8 minutes, and preferably up to about 5 minutes, after mixing with the aqueous medium. Like the tacky states, the putty state is dependant on a number of factors including the relative ratio of the components, the presence of additives, the particle size of the components and the like. Because the items to be affixed can be repositioned during the tacky state or the compositions can be shaped during the putty state, this combined time of the tacky state and the putty state is some times referred to as the working time. Typical compositions have a working time of up to 8 minutes from initial mixing and often the working time is up to about 5 minutes after which time the compositions have sufficiently begun hardening that further manipulation will result in degradation of ultimate strength of the bond.

After the putty state, the compositions harden like a cement to form a substantially permanent bond between the materials. In the cement state, the composition hardens and the materials that have been affixed to each other cannot be separated without the application of significant force. The compositions typically will begin to harden within about 8 minutes, and often within about 5 minutes, after mixing with the aqueous medium. The amount of time to reach the cement state is also dependant of the same factors listed above.

A further important property of the compositions is that these compositions have significant coherency and integrity within a wet environment. In the medical field, this would include a surgical site, a wound or similar situation where blood and other bodily fluids are present. The tacky state, the putty state and the cement state all occur in either a wet environment or in a dry environment. In order to get the desirable properties, the user need not ensure that the application site is clean and dry. In a wet environment, the compositions tend to remain together and the presence of the liquid does not significantly affect the integrity of the composition or the ultimate strength properties.

As noted above, the compositions have a tacky state shortly after initial mixing. This tacky state enables two items, such as bone and another material, to be held together by the composition itself, without the need for external force, until the composition sets to the final hardened cement state. The amount of force needed to remove two opposed pieces of material from each other is the separation strength. For the composition as described herein, these compositions have a separation strength during the tacky state within the first 4 minutes and preferably within the first 2 minutes after initial mixing from about 10 kPa to about 250 kPa and preferably from about 50 kPa to about 150 kPa. For certain applications it may be useful to have a longer tack state whereby certain compositions have a separation strength which continues in this range for up to 12 minutes. This separation strength is sufficiently high that the items to be joined need not be held together unless there is an apposing strength of the items greater than the separation strength and also, the items can still be repositioned or even reapposed without loss of ultimate bond strength.

Factors that may affect the length of the tacky state, the length of the putty states and the ultimate cure time, as well as strength properties of the compositions include: the percentage (w/w) TTCP and the compounds that are structurally similar to phosphoserine based solely on the weight of the TTCP and the compounds that are structurally similar to phosphoserine in the composition, the selection of the compounds that are structurally similar to phosphoserine, the particle size of the TTCP, and the nature and quantity of any additives and/or fillers which may be combined to the composition to enhance the material properties.

The mean particle size of the TTCP should be below 1000 μm, preferably 1-250 μm, most preferably 10-100 μm. As the mean particle size of the TTCP is reduced, the TTCP tends to dissolve too fast and these compositions may not be practical for all uses as disclosed herein. On the other hand if the TTCP has a mean particle size of greater than about 1000 μm, the intra-operative performance of the compositions may not have the desired initial strength and be too slow to set. If a longer working time is desired, then TTCP with a larger mean particle size can be used; however, if a shorter working time is desired, then TTCP with a smaller mean particle sizes can be used. In certain use environments, compositions that have a multi-modal mean particle size distribution with, for example, one mode less then 50 μm and the other mode above 50 μm can provide unique properties such as a fast initial cure rate from the smaller mean particle size mode combined with higher intrinsic compression strength of the material from the larger mean particle size mode. The TTCP may also be a solid mass or a coating of TTCP on a substrate.

The aqueous based mixing media useful for combining the TTCP and compound that is structurally similar to phosphoserine powders can include water, buffers such as sodium phosphate, saline, and blood based products such as whole blood, plasma, platelet rich plasma, serum, and/or bone marrow aspirate. The blood based products are used with the goal of achieving enhanced rate of bone healing and remodeling. It is also possible to use the compositions without premixing with an aqueous medium if the composition is to be used in a sufficiently wet environment that the aqueous medium can be absorbed from the in situ site. In this situation, the composition can be dusted on or other wise applied to the desired site and then mixed with the liquids that are already present at the site.

Additives may enhance the material properties. These properties include the handling, porosity, intrinsic material strength, & bone healing rate (osteogenic). Suitable additives include: alpha or beta tri-calcium phosphate (α-TCP or β-TCP), calcium sulfate, calcium silicate, calcium carbonate, sodium bicarbonate, sodium chloride, potassium chloride glycerol phosphate disodium, amino acids such as serine, excess amounts of phosphoserine, polyols (such as glycerol, mannitol, sorbitol, trehalose, lactose, & sucrose), silk, keratin (primarily found in human hair), autologous bone powder or chips, demineralized bone powder or chips, collagen, various biodegradable polymers such as poly ethylene glycol (PEG), poly lactic acid (PLLA), poly glycolic acid (PGA), and copolymers of lactic and glycolic acid (PLGA), further including biodegradable block polymers such as poly lactic acid (PLLA)-polyethylene glycol (PEG)-poly lactic acid (PLLA) block polymer, BMP7, stem cells, parathyroid hormone (PTH), bisphosphonates, and mixtures thereof. In addition, other additives and/or fillers could be incorporated which offer surgical visual aids & anti-infective properties.

While not wishing to be bound by theory, compositions of the present disclosure are believed to function as follows: the TTCP, which is basic in nature, reacts with the compound that is structurally similar to phosphoserine, which is acidic in nature, upon mixing with the aqueous medium and forms a hardened, layered structure upon curing. This reaction is exothermic; the degree of exothermic activity depends on a number of factors including the volume of the composition. The low pH nature of the compounds that are structurally similar to phosphoserine enable the hydroxyl of phosphate or phosphonate and COOH functional group to bond through ionic interaction with the calcium ions from within the TTCP. This resulting reactive intermediate continues a cascade of ionic interactions with calcium and phosphate ions within the TTCP or HA on the bone surface or any other metal ions of the metal implants. This series of interactions provides transient material having the tacky properties while curing and the adhesion strength that increases upon cure.

The compositions when mixed with aqueous medium typically have a creamy or a tacky paste consistency initially. Also, the mixing of the compositions with the aqueous medium does not require a high level of force or shear and simple hand mixing, such as with a spatula, is sufficient in most instances. It is envisioned that the present compositions may be applied via injection through a syringe or other suitable pressurized implement, applied with a spatula, and as otherwise desirable by a user. The creamy or tacky viscosity allows for application of the composition to the defect site for a defined period of time. The compositions allow the bone to be repositioned several times within 4 minutes and preferably within 2 minutes without losing tack properties. If the compositions need to be injected through a syringe or cannula, the viscosity of the composition during the working time can be important. For these situations, viscosities of the compositions herein should be preferably below about 150 centipoise.

Still further embodiments have a consistency similar to putty. These compositions hold their cohesive, tacky, and sculpting properties over a longer period of time even when subjected to a wet field. The compositions have working time for sculpting sometimes up to 15 minutes depending on the application requirement, typically up to about 8 minutes, and preferably up to about 5 minutes, after mixing with the aqueous medium. Formulations with an increased amount of compound that is structurally similar to phosphoserine greater than 25% w/w or increased TTCP mean particle size greater than about 250 microns tend to have longer working times and seem to be suitable for use in situations where the putty will fill defects in structures that are well supported by surrounding bone. In these situations the putty does not need to harden as fast provided it maintains its cohesive properties in the wet field. Another property of the compositions is that the compositions will adhere to themselves as well as to an external surface such as bone. This is useful in situations where a shape is formed during the putty state and this shape can then adhere to bone. Also, in some instances a user may apply a mass of the composition to a bone or other surface and then shape the composition into the final desired shape during the working time of the composition.

In addition other suitable adhesives include polymethyl methacrylate based adhesives, collagen based adhesives, fibrin based adhesives, hyaluronic acid based adhesives, gelatin based adhesives and PEG based hydrogel adhesives.

An important property of the adhesive is the separation strength as described above. Suitable adhesives have separation strength of at least about 30 N and preferably have a strength of between about 80 and about 180 N. Particularly preferred adhesives include those that incorporate phosphoserine (OPLS), TTCP and other components such as PLGA (poly (lactic/glycolic acid)) fibers of various ratios of lactic and glycolic acid.

Fibers can be used in the adhesive composition to increase the material intrinsic strength. An important aspect for chemical ion-dipole adhesion of these fibers is the size and/or surface area. The size or surface area can be defined by the aspect ratio (length:diameter). The preferred aspect ratio is from 2:1 to 50:1; more preferable from 10:1 to 35:1. The overall length of the fiber can be up to 5 mm; however, since the material could be used as bone to bone adhesive, the length of the fiber may be more appropriate at lengths that are less than this. The fiber may be any type of fiber that is suitable for use in a surgical setting. Examples include copolymers of lactic acid and glycolic acid with a lactic acid glycolic acid ratio of between 5:95 and 70:30. Other examples include silk, keratin, collagen, autologous bone powder or chips, demineralized bone powder or chips, calcium silicate, calcium sulfate, biodegradable polymers (such as PLLA, PGA, PLGA) or biodegradable block polymers (such as PLLA-PEG-PLLA), also granules made from calcium sulphate, α-TCP, β-TCP or hybrids thereof.

Examples of suitable adhesives are shown below in table 1.

TABLE 1

| Formulation | Test Configuration | Failure Load |
| --- | --- | --- |
| 1A | | |
| TTCP = 400 mg, OPLS = 330 mg PLGA fibers = 62.5 mg Water = 165 microliters | Titanium plate on cortical bone | 141 N |
| 1B | | |
| TTCP = 400 mg, OPLS = 400 mg PLGA fibers = 62.5 mg Water = 180 microliters | Titanium plate on cortical bone | 165 N |
| 1C | | |
| TTCP = 400 mg, OPLS = 330 mg PLGA fibers = 62.5 mg Water = 165 microliters | Suture on cortical bone | 76 N |

Note:
PLGA Fibers = 4 mm length, 200 micron diameter, Lactic: Glycolic ratio of 10:90

The amount of adhesive that is used is not particularly important so long as sufficient adhesive is used to form a strong enough bond between the sheet 22 and the bone to hold the suture 26 in place and prevent the suture anchor 20 from moving while the patient undergoes normal activity. Typically sufficient adhesive is used so that it is not necessary to form a groove between the holes 24 to form a relief area for the suture 26. The suture 26 will press into the adhesive that is placed between the sheet 22 and the bone and form a cohesive bond.

Because the suture anchor 20 is attached to the bone by use of an adhesive, there is minimal invasion of bone structure. This can be particularly advantageous in situations where the patient has bones that are compromised in some fashion due to age or medical condition. Even for patients with normal bone density, the use of a non-invasive attachment method and device for sutures reduces the risk of post procedure complications. As will be discussed hereinafter, certain embodiments of the present disclosure may minimally invade the outer surface of the bone but even these minimal invasions provide significant advantages for patients with compromised bone structure and density and for minimizing post procedure complications.

Referring to FIGS. 4 and 5, a suture anchor 40 has a sheet 42. On the top surface of sheet 42 is an eyelet 44 that has an opening 48 though which a suture 26 can pass. The sheet 42 can be formed from any of the same materials as discussed above and eyelet 44 has the advantage that the suture 46 can be attached after the suture anchor is affixed to the bone.

Typically the suture 46 will be tied to eyelet 44 prior to being used to adhere the soft tissue in position next to the bone.

FIG. 6 shows a bottom view of a suture anchor 50 that has a sheet 52 with at least two holes 54 through sheet 52. The bottom surface of sheet 52 has a series of protrusions 56 that in one embodiment have been punched through sheet 52. Protrusions 56 extend downward from the bottom surface of sheet 52 and it is preferred that the size of the protrusions will extend only into the adhesive that is placed between suture anchor 50 and not into the surface of the bone. In a further embodiment, the protrusions 56 are larger, and the protrusions 56 can penetrate a short distance into the outer surface of the bone. In this embodiment, some pressure or impact will be needed to seat the protrusions 56 into the bone. This can be done in any conventional manner. Although FIG. 6 shows the protrusions placed downwards toward the bone, the structure can also be installed with the protrusions 56 facing upwards away from the bone. In this case, the adhesive will also be placed over plate 52 as well as between the plate 52 and the bone.

Figure 6A:
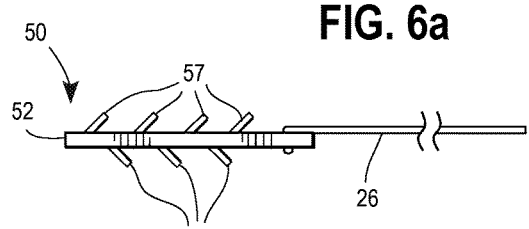
FIG. 6a shows a side view of an alternate embodiment of FIG. 6.
Figure 6B:
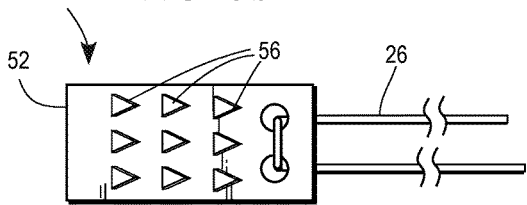
FIG. 6b show a side view of a further alternate embodiment of FIG. 6.
Figure 6C:
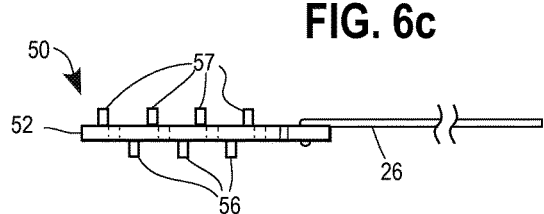
FIG. 6c shows a side view of a further alternate embodiment of FIG. 6.
Figure 6D:
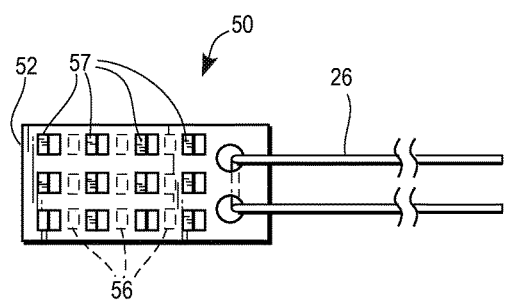
FIG. 6d shows a side view of a further alternate embodiment of FIG. 6.

FIG. 6a shows a further embodiment where the sheet 52 has protrusions 56 extending downward and protrusions 57 extending upward. In this embodiment, the size of protrusions 56 and 57 are similar to those described relative to FIG. 6. FIG. 6b shows a still further embodiment where the sheet 52 has rectangular protrusions 58 extending downward and rectangular protrusions 59 extending upward. As shown the protrusions 56, 57, 58, and 59 can angle toward the suture 26 so that the protrusions will further grab the adhesive as tension is placed on the suture 26.

Figure 8:
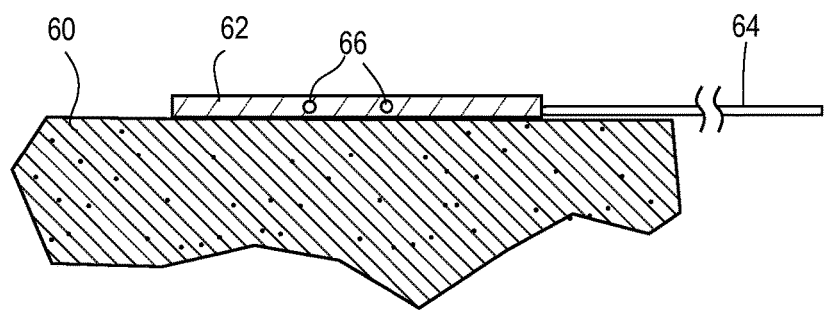
FIG. 8 is a partly broken away view of the embodiment of FIG. 7 taken along line 8-8.

FIGS. 7 and 8 show a further embodiment of the method of the present disclosure. In the embodiment shown in FIGS. 7 and 8, no separate suture anchor is used. Instead, the bone 60 will have an area of adhesive 62 placed on the bone 60. Sufficient adhesive 62 is used to create a large enough area to securely hold suture 64. In some embodiments, the suture 64 is either looped to form a loop 66 or knotted to increase the surface area contact between the adhesive 62 and the suture 64. In another embodiment as shown in FIG. 7a, at least one end of the suture 64 is braided such that it forms a net 68 to create a larger surface area. In addition to the net shown, other braided shapes can also be used to create a large surface area. Non-limiting examples include a mesh area 68a or a straight braided area 68b as shown in FIGS. 7b and 7c. FIG. 7d is an enlargement of the braided areas of FIG. 7c. Although FIG. 7c shows the braiding covering the entire circular area, it also possible that the braided area is only around the circumference of the area and that the center portion is left open.

One advantage of this particular method is that less foreign material is introduced into the body as part of the procedure because no plate is used. Typically about 0.5 g grams of adhesive 62 have been found to form a suitable bond between the bone 60 and the suture 64. The amount of adhesive 64 used should be large enough to cover the suture 64 and hold it in place against the bone 60 but small enough so that the adhesive 62 will set quickly. The exact amount of adhesive used is not important so long as sufficient adhesive 62 is used to secure the suture 64 to the bone.

The amount of time needed for the adhesive to set to the required separation strength will depend in part on the particular adhesive formulation used. Typically, the adhesive should set sufficiently quickly so that the surgeon will not have to wait to attach the soft tissue to the bone, often less than 10 minutes. It is recognized that the adhesive may set initially to a strength level sufficient to enable the surgeon to suture to soft tissue to the bone and that the adhesive will continue to set over time until the adhesive reaches its maximum strength. For most adhesives that are suitable for use in the present disclosure, within 30 minutes the adhesive will set to a strength of at least 90% of the final strength.

Figure 9:
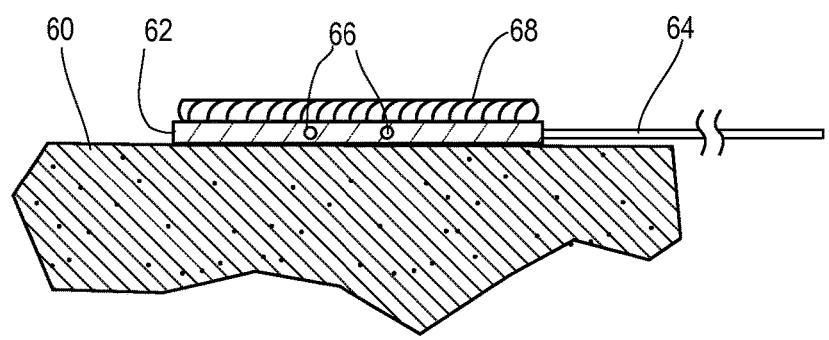
FIG. 9 is a view similar to FIG. 8 showing an alternative embodiment.

In FIG. 9 one further embodiment of the method of the present disclosure is illustrated. In this embodiment a sheet 70 is placed on top of the adhesive 62 that already has the suture 64 placed in the adhesive 62. The sheet 70 will protect the adhesive 62 and provide added surface area for the adhesive 62 to adhere. By increasing the surface area, this increases the purchase of the resulting bond and makes the suture 64 even more secure.

Typically, the components will be provided to the end user as a kit that includes adhesive premix, adhesive liquid, and an anchor sheet. In some embodiments, the sutures can also be provided in the same kit or because of the varying need for different suture sizes, the sutures can be provided separately.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A method of affixing a suture to the outer surface of a bone in a minimally invasive manner comprising applying an adhesive to the outer surface of the bone; and bonding the suture onto the outer surface of the bone, wherein the adhesive comprises a calcium phosphate and a compound of the following formula:

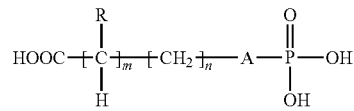

where A is O, $CH_2$, or S; R is H, $NH_2$, $NHCO(CH_2)_tCH_3$ where t is 0 to 2, $NH(CH_2)_xCH_3$ where x is 0 to 3, $NR_1R_2$ where $R_1$ is $(CH_2)_yCH_3$ and $R_2$ is $(CH_2)_yCH_3$ where y is 0 to 2, $(CH_2)_zCH_3$ where z is 0 to 3; m is 0 to 1; and n is 0 to 3; and when set, the adhesive has a separation force of greater than or equal to about 30 N.

2. The method of claim 1, wherein the adhesive comprises tetracalcium phosphate, phosphoserine, and water.

3. The method of claim 2, wherein:

the adhesive has a tack state for up to about 12 minutes after the tetracalcium phosphate and phosphoserine are mixed with the water;

has a separation strength in the range of about 10 kPa to about 250 kPa during the tack state;

has a putty state for up to about 15 minutes after the tetracalcium phosphate and phosphoserine are mixed with the water and has an adhesive strength upon curing of greater than 250 kPa.

4. The method of claim 2, wherein the adhesive further includes a fiber.

5. The method of claim 1, wherein the suture is threaded through a sheet and the sheet is adhesively bonded to the bone.

6. The method of claim 1, wherein the suture is affixed to the bone through a suture anchor.

7. The method of claim 1, wherein the suture is affixed to the bone without a suture anchor.

8. The method of claim 1, wherein at least one end of the suture comprises a braided or looped shape that extends into the adhesive.

9. The method of claim 1, wherein the method requires minimal invasion of the outer surface of the bone.

10. A method of attaching a suture anchor to the outer surface of bone comprising: applying an adhesive to the outer surface of a bone; and bonding the suture anchor to the outer surface of the bone, wherein the suture anchor comprises a relatively flat sheet and a suture attached to the sheet, and the adhesive comprises a calcium phosphate and a compound of the following formula:

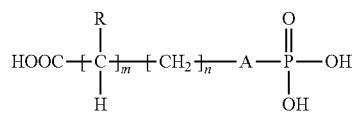

where A is O, $CH_2$, or S; R is H, $NH_2$, $NHCO(CH_2)_t CH_3$ where t is 0 to 2, $NH(CH_2)_x CH_3$ where x is 0 to 3, $NR_1 R_2$ where $R_1$ is $(CH_2)_y CH_3$ and $R_2$ is $(CH_2)_y CH_3$ where y is 0 to 2, $(CH_2)_z CH_3$ where z is 0 to 3; m is 0 to 1; and n is 0 to 3.

11. The method of claim 10, wherein the sheet has one side that is roughened.

12. The method of claim 10, wherein the sheet has protrusions extending from one side of the sheet.

13. The method of claim 12, at least one protrusion extends into the adhesive.

14. The method of claim 12, wherein at least one protrusion has a pointed shape or a rectangular shape.

15. The method of claim 10, wherein the sheet comprises a material selected from the following group: titanium, a titanium alloy, a ferrous alloy, a cobalt-chromium alloy, a degradable metal, a biocompatible polymer, a bioceramic, or a composite of a polymer and a ceramic.

16. The method of claim 10, wherein the sheet has an opening and optionally comprises at least one eyelet that extends from the top of the sheet.

17. The method of claim 10, wherein the sheet has a smooth surface.

* * * * *